(12) United States Patent
Kim et al.

(10) Patent No.: US 7,615,366 B2
(45) Date of Patent: Nov. 10, 2009

(54) BACILLUS AMYLOLIQUEFACIENS KTGB0202 AND CONTROL METHOD OF PLANT PATHOGENIC FUNGI USING THAT

(75) Inventors: Kab-Sig Kim, Deaejeon (KR); Woon-Hyung Yeo, Daejeon (KR)

(73) Assignee: KT & G Co., Ltd., Daejeon (KR)

( * ) Notice: Subject to any disclaimer, the term of this patent is extended or adjusted under 35 U.S.C. 154(b) by 502 days.

(21) Appl. No.: 10/583,076

(22) PCT Filed: Dec. 7, 2004

(86) PCT No.: PCT/KR2004/003203

§ 371 (c)(1), (2), (4) Date: Jun. 15, 2006

(87) PCT Pub. No.: WO2005/059112

PCT Pub. Date: Jun. 30, 2005

(65) Prior Publication Data

US 2008/0102062 A1 May 1, 2008

(30) Foreign Application Priority Data

Dec. 17, 2003 (KR) ...................... 10-2003-0092300

(51) Int. Cl.
*A01N 25/00* (2006.01)
*C12N 1/20* (2006.01)

(52) U.S. Cl. ..................... 435/252.5; 435/832; 424/405; 424/93.46

(58) Field of Classification Search ........................ None
See application file for complete search history.

(56) References Cited

U.S. PATENT DOCUMENTS 5,750,386 A * 5/1998 Conkling et al. ............ 800/279

* cited by examiner

*Primary Examiner*—David M. Naff
*Assistant Examiner*—Debbie K Ware
(74) *Attorney, Agent, or Firm*—John K. Park; Park Law Firm (57) ABSTRACT

The present invention relates to a novel microorganism *Bacillus amyloliquefaciens* KTGB0202 and a method for controlling plant pathogens using the same. More particularly, the present invention relates to a novel microorganism *Bacillus amyloliquefaciens* KTGB0202 (accession number: KCTC 10564BP) bacterium which has an excellent control effect against crop powdery mildew and a broad spectrum of antifungal activity against plant pathogenic fungi and inhibits tobacco mosaic virus infection, as well as an eco-friendly bacterial culture broth for controlling powdery mildew, which contains the same. Also, the present invention relates to antifungal substance KTGB0202AFO1 obtained by extraction and purification from the *Bacillus amyloliquefaciens* KTGB0202 bacteria. The inventive *Bacillus amyloliquefaciens* KTGB0202 bacteria have a broad spectrum of antifungal activity, and are excellent in activity continuance and used for controlling various plant pathogens, including powdery mildew.

5 Claims, 2 Drawing Sheets

_BACILLUS AMYLOLIQUEFACIENS_ KTGB0202 AND CONTROL METHOD OF PLANT PATHOGENIC FUNGI USING THAT

TECHNICAL FIELD

The present invention relates a novel microorganism _Bacillus amyloliquefaciens_ KTGB0202 and a method for controlling plant pathogens using the same.

More particularly, the present invention relates to a microbial pesticide containing the _Bacillus amyloliquefaciens_ KTGB0202 bacteria, which is inexpensive and safe, and at the same time, has an excellent control effect against powdery mildew, _Cladosporium_ sp., _Colletotrichum_ sp, _Phytophthora_ sp., _Botrytis cinerea, Rhizoctonia solani, Fusarium_ sp., _Alternaria_ sp., _Magnaporthe grisea, Puccinia recondita, Corticium sasaki, Candida_ sp. and the like, as well as a method for controlling plant pathogens using the KTGB0202 bacteria.

BACKGROUND ART

Currently, chemically synthesized agricultural chemicals are mainly used to control and inhibit the development of plant pathogens.

However, such agrochemicals are limited in use since they lead to the destruction of the natural ecosystem and have a very high possibility to cause the chemical poisoning, carcinogensis, malformation and various diseases of the human body due to residual toxicity.

For this reason, studies on the development of low toxic, eco-friendly biological agrochemicals are now actively being conducted.

Korean Patent Registration No. 10-0257452 (entitled "a _bacillus subtilis_ A405 strain producing an antibacterial peptide with plant disease control activity and a method for controlling plant diseases using the same) discloses a _Bacillus subtilis_ A405 strain (KFCC-11024) producing an antibacterial peptide with plant disease control activity, and a method for controlling plant diseases characterized by spreading a microbial formulation containing this strain to the crop field to be controlled.

Meanwhile, powdery mildew is one of the main plant diseases, which develop and cause great damages to crops, such as strawberries, cucumbers and the like, which become the main income source of farmhouses. Particularly recently, fungi resistant to the existing agrochemicals frequently appear so often that controls of plant diseases only by chemical treatment methods encounter limitations in their effect.

Thus, in an attempt to control powdery mildew using biopesticides, methods using natural substances, microorganisms and the like have been suggested.

Korean Patent Laid-Open Publication No. 2002-0072813 (entitled "New _Bacillus_ sp. CMB26 strain, production of lipopeptide using CMB26 strain, and germicide of plant fungal pathogens containing CMB26 strain and/or lipopeptide) discloses a novel microorganism _bacillus_ sp. CMB26 (KFCC-11289) characterized by producing lipopeptide with the high activity to disable the spores and mycelia of molds, and an antifungal agent against plant mold fungi such as powdery mildew, _Mycosphaerella melonis, Botryosphaeria dothidea, Fusarium oxysporum, Collectotrichum gloeosporum, Botrytis cinerea, phytophthora_ root rot, or _Rhizoctonia solani_.

However, although a number of biological control agents showing antifungal activity in _Bacillus_ sp. fungi as described above are now published, there is no report on microbial pesticide containing a _Bacillus amyloliquefaciens_ strain, which has an excellent control effect against plant pathogens and at the same time, is inexpensive and safe.

DISCLOSURE OF INVENTION

The present invention has been made to solve the above-described problems occurring in the prior art, and it is an object of the present invention to provide a novel _Bacillus amyloliquefaciens_ KTGB0202 having a control effect against plant pathogens.

Another object of the present invention is to provide an biopesticide for the control of plant pathogens, including powdery mildew, which contains the novel _Bacillus amyloliquefaciens_ KTGB0202, and thus, has broad antifungal activity, is excellent in activity continuance and physically and chemically safe, as well as a method for controlling plant pathogens using the KTGB0202 strain.

The present invention relates to a novel _Bacillus amyloliquefaciens_ KTGB0202 and a method for controlling plant pathogens using the same.

The present invention provides a novel microorganism _Bacillus amyloliquefaciens_ KTGB0202 (accession number: KCTC 10564BP) which is excellent in a control effect against powdery mildew occurring in various crops, has a broad spectrum of antifungal activity against plant pathogens and inhibits tobacco mosaic virus infection.

Also, the present invention provides KTGB0202-AF01, a novel antifungal active substance, which is produced by the inventive _Bacillus amyloliquefaciens_ KTGB0202.

Also, the present invention provides a bacterial culture broth containing the _Bacillus amyloliquefaciens_ KTGB0202 bacteria, for use in eco-friendly controlling powdery mildew.

The _Bacillus amyloliquefaciens_ KTGB0202 bacteria according to the present invention do not form special pigments, and the temperature suitable for their growth is 27-30° C.

Figure 1:
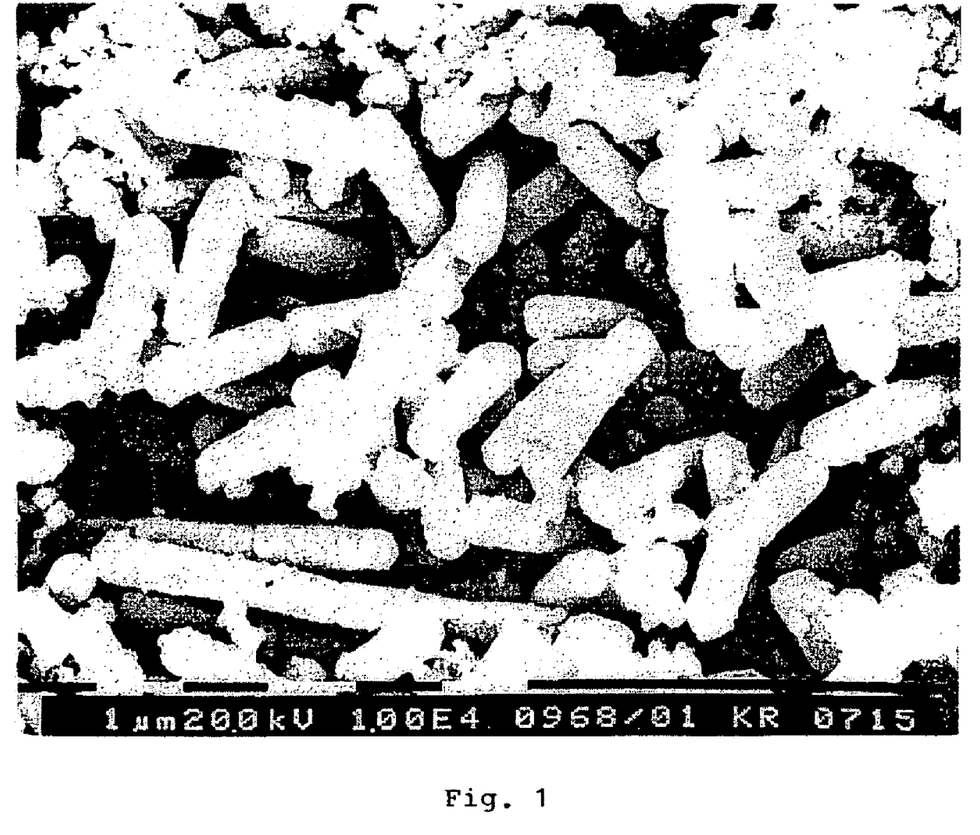
FIG. 1 is an electron microscopic photograph showing the inventive KTGB0202 bacteria.

Furthermore, the inventive KTGB0202 bacteria are Gram-positive, aerobic, mobile rod-shaped bacteria with a size of 0.8-1.0 μm×1.5-2.0 μm, which secrete catalase enzyme (see FIG. 1).

Meanwhile, the results of analysis for the cell fatty acids of such bacteria are shown in Table 1 below.

The base sequence of the KTGB0202 bacteria determined by gyrase subunit A gene analysis is shown in SEQ ID NO: 1.

The novel bacterial strain according to the present invention was termed "_Bacillus amyloliquefaciens_ KTGB0202" and deposited under the accession number KCTC 10564BP on Dec. 10, 2003 with the Korean Collection for Type Cultures (KCTC), Korean Research Institute of Bioscience and Biotechnology (KRIBB).

A culture process for obtaining a culture having antifungal activities against powdery mildew and other plant pathogens, from the inventive _Bacillus amyloliquefaciens_ KTGB0202 bacteria, may be performed in nutrient agar medium, potato sucrose agar medium or Mueller Hinton agar medium.

Plant pathogens which can be controlled by the inventive _Bacillus amyloliquefaciens_ KTGB0202 bacteria include Powdery mildew, _Cladosporium_ sp., _Colletotrichum_ sp., _Phytophthora_ sp., _Botrytis cinerea, Rhizoctonia solani, Fusarium_ sp., _Alternaria_ sp., _Magnaporthe grisea, Puccinia recondita, Corticium sasaki_, and _Candida_ sp.

The inventive _Bacillus amyloliquefaciens_ KTGB0202 bacteria are stable at a high temperature of more than 80° C., and their control activity against powdery mildew when stored at room temperature in culture solution conditions is maintained for at least 6 months.

The inventive *Bacillus amyloliquefaciens* KTGB0202 bacteria are more effective in controlling powdery mildew fungi, including *Sphaerotheca fuliginea* of gourd plants, *S. humuli* of strawberry, *S. pannosa* of rose, *Erysiphe tabacina* of tobacco, *Leveillula taurica* and *Erysiphe cichoracearum* of Solanaceae vegetables, *Leveillula heraclei* of carrots, and *Blumeria graminis* of barley.

A plant virus against which the inventive *Bacillus amyloliquefaciens* KTGB0202 bacteria has infection inhibitory activity is tobacco mosaic virus (TMV).

Moreover, an antifungal active substance in culture solution which is produced by the inventive KTGB0202 is isolated by fat-soluble resin, and purified by silica gel chromatography and LH-20 gel chromatography so as to obtain a white powdery substance. This antifungal substance was termed "KTGB0202-AF01".

Figure 2:
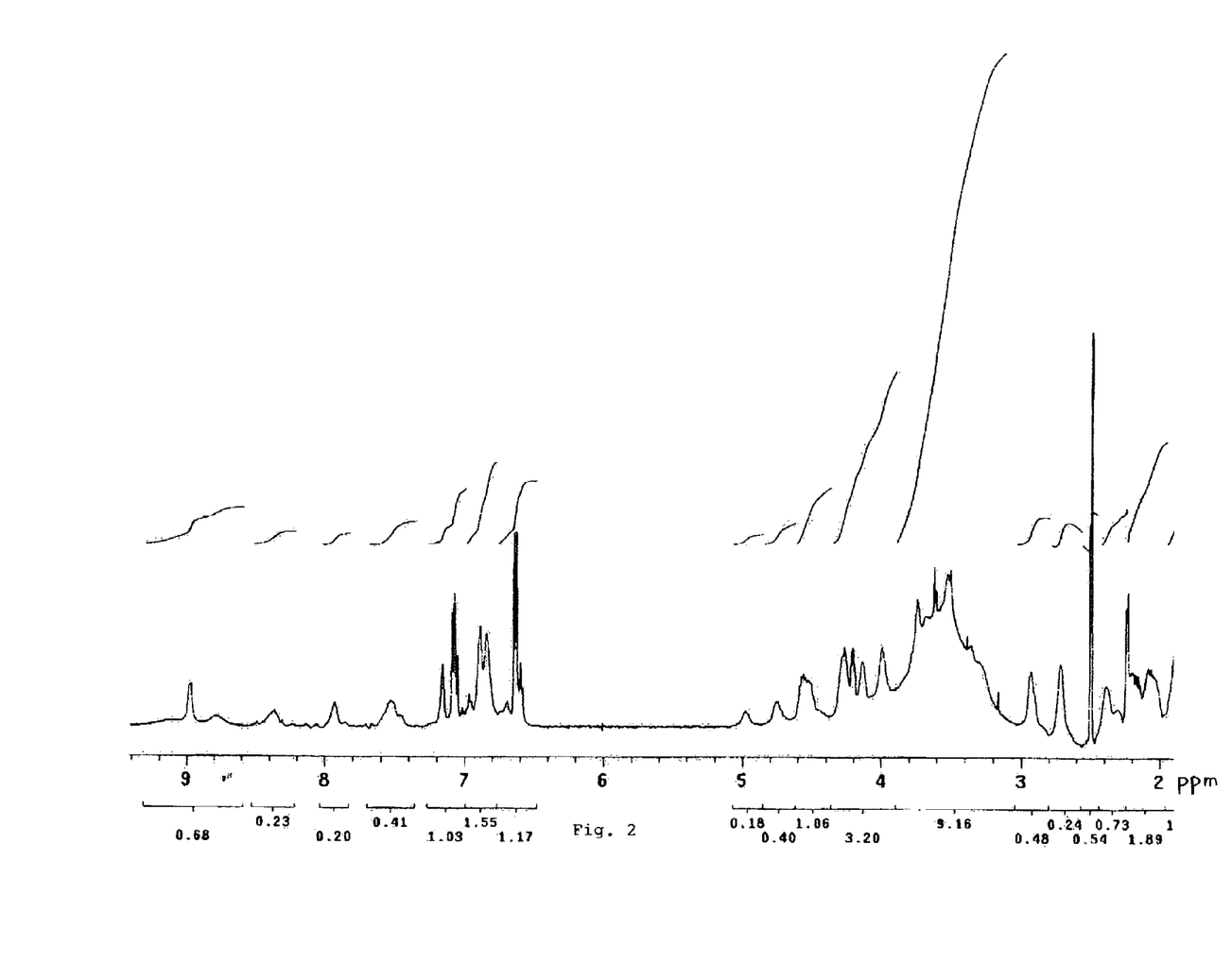
FIG. 2 shows the $^1$H-NMR spectrum for the antifungal substance KTGB0202-AF01 obtained by extraction and purification from the inventive KTGB0202 bacteria.

The $^1$H-NMR spectrum for the antifungal active substance is shown in FIG. 2.

According to the present invention, the novel *Bacillus amyloliquefaciens* KTGB0202 having a control effect against plant pathogenic fungi is provided.

Furthermore, the present invention provides a biopesticide for controlling plant pathogens, including powdery mildew, which contains the *bacillus amyloliquefaciens* KTGB0202 microorganisms, and thus, has broad antifungal activity, is excellent in activity continuance, and is physically and chemically safe, as well as a method for controlling plant pathogenic fungi using the KTGB0202 microorganisms.

Moreover, the present invention provides the antifungal active substance KTGB0202-AF01 produced by the novel KTGB0202 microorganisms. Also, the present invention provides a biopesticide for controlling plant pathogens, including powdery mildew, which contains the KTGB0202-AF01 microorganisms, and thus, has a broad antifungal activity with an excellent activity continuance, as well as a method for controlling plant pathogens using the microorganisms.

BEST MODE FOR CARRYING OUT THE INVENTION

Example 1

Isolation and Identification of *Bacillus amyloliquefaciens* KTGB0202 Bacteria

The leaves of oak trees growing naturally on hills in the vicinity of KT&G Central Research Institute located at Shinsong-Dong, Yusong-Ku, Taejon, Korea, were collected.

The collected leaves were washed with water, dried in air, surface-sterilized with 1% sodium hypochlorite, sufficiently ground with a pestle and mortar, and diluted in distilled water.

The dilution was plated on Mueller Hinton agar medium using the bilayer method, and cultured in an incubator at 27° C. for 2-3 days. Then, a single bacterial colony was purely isolated by several subcultures.

The identification of a strain for the single isolate was performed by morphological observation and the analysis of physiological characteristics, cell fatty acids and 16S rDNA base sequences.

This strain grows well in nutrient agar medium, potato sucrose agar medium and Mueller Hinton agar medium. Also, it does not form special pigments, and the temperature suitable for its growth is 27-30° C.

Furthermore, the strain is Gram-positive, aerobic, mobile rod-shaped bacterium with a size of 0.8-1.0 μm×1.5-2.0 μm, which secretes catalase enzyme (see FIG. 1).

The results of analysis for the cell fatty acids are given in Table 1 below.

TABLE 1

| The fatty acids composition analysis of KTGB0202 bacteria | |
|---|---|
| Fatty acid composition | KTGB0202 microorganism |
| C14:0 ISO | 1.06 |
| C14:0 | 1.02 |
| C15:0 ISO | 20.39 |
| C15:0 ANTEISO | 43.73 |
| C16:0 ISO | 2.95 |
| C16:1 w1 1c | 1.35 |
| C16:0 | 7.53 |
| C17:0 ISO | 8.00 |
| C17:0 ANTEISO | 11.96 |

The base sequence of the identified strain determined by gyrase subunit A gene analysis is shown in SEQ ID NO: 1 in the attached sequence list.

Considering the above results collectively, *Bacillus amyloliquefaciens* was identified and termed "KTGB0202 strain".

The isolated and identified strain was deposited under the accession number KCTC 10564BP on Dec. 10, 2003 with the Korean Collection for Type Cultures (KCTC), Korean Research Institute of Bioscience and Biotechnology (KRIBB), which is an International Depository Authority for patent application.

Hereinafter, the present invention will be described by the following examples and test examples, but these examples are not construed to limit the scope of the present invention.

Example 2

Culture of *Bacillus amyloliquefaciens* KTGB0202 Strain

The *Bacillus amyloliquefaciens* KTGB0202 strain of Example 1 was prepared.

A Mueller Hinton agar medium was prepared.

21 g of the prepared Mueller Hinton agar medium was dissolved well in 1 liter of distilled water, and the solution was dispensed into 500-ml erlenmeyer flask at 200 ml each time, and sterilized in 1.5 atms at 121° C. for 20 minutes.

The KTGB0202 bacteria in a plate state was taken by a platinum wire and inoculated into the prepared medium. The inoculated bacteria were cultured at 27° C. for 4 days with shaking at 110 rpm.

The culture medium showed a weak yellow color, was viscose, and had a pH of 6.79.

Example 3

Isolation and Purification of Antifungal Substance KTGB0202-AF01 Produced by KTGB0202 Bacteria The *Bacillus amyloliquefaciens* KTGB0202 bacteria-containing culture of Example 2 was prepared.

The prepared culture was passed through a glass column filled with Diaion-HP10 resin.

The antifungal substance adsorbed onto the column was extracted with 70% aqueous acetone and concentrated.

The concentrated substance was dissolved in a small amount of chloroform (CHCL$_3$) and methanol (MeOH) and subjected to silica gel column chromatography.

While gradually increasing the polarity of the solvent system from 7:3 to 0:1, the active substance was developed to purify a substance showing the strongest activity at a polarity range of 3:7 to 1:9.

The purified substance was concentrated under reduced pressure, dissolved in a small amount of methanol, and finally purified by LH-20 (Sephadex LH-20) gel chromatography using the same solvent as a developing solvent.

The finally purified substance was insoluble in nonpolar solvents such as ethyl acetate (EtoAc), chloroform (CHCl$_3$) and the like, and slightly soluble in methanol. Also, it was well soluble in a 1:1 mixture solution of chloroform and methanol and in water.

The $^1$H-NMR spectrum for the above active substance is shown in FIG. 2.

Test Example 1

Measurement of Change in Activity of KTGB0202 Bacteria during Culture Time

In order to examine changes in antifungal, antiviral and powdery mildew control effects during culture time, the KTGB0202 bacteria was cultured in Mueller Hinton agar medium at conditions of 27° C. and 110 rpm, during which samples were taken at different points of time and measured for activity.

The antifungal effect was measured by a paper disc method on tomato *Cladosporium* sp., and the antiviral effect was examined by a pretreatment method on Xanthi-nc tobacco leaves.

To measure the powdery mildew control effect, a five-fold dilution was spread to leaves three times at five-day intervals, and after 7 days, the results was examined and shown in Table 2 below.

Also, the bacterial count reached the highest level upon 48-72 hours of culture.

Test Example 2

Test of Inhibitory Effect against Tobacco Mosaic Virus (TMV) Infection with Change in Concentration of KTGB0202 Bacteria Culture The KTGB0202 strain-containing Mueller Hinton liquid medium prepared in Example 1 was centrifuged at 10,000 rpm for 15 minutes into a supernatant and cells, diluted in sterilized distilled water, and treated by spreading with a brush to Xanthi-nc tobacco leaves.

After one day of treatment, TMV were inoculated and the infection inhibitory effect of the KTGB0202 bacteria culture on viral infection was examined as shown in Table 3 below.

TABLE 3

| Inhibitory activity of KTGB0202 on tobacco mosaic virus infection | |
|---|---|
| Tested substance | Virus infection inhibitory effect (%) |
| Undiluted culture | 98 |
| Two-fold-diluted culture | 95 |
| Ten-fold-diluted culture | 70 |
| Twenty-fold-diluted culture | 50 |
| Fifty-fold-diluted culture | 20 |
| Tap water | 0 |

As can be seen in Table 3, the virus infection inhibitory effect of the KTGB0202 bacteria culture according to the present invention was remarkably reduced from the ten-fold dilution.

Test Example 3

Test of Antifungal Activity of KTGB0202 Bacteria

The KTGB0202 strain prepared in Example 1 was cultured in Mueller Hinton agar medium for 3-4 days and made into an

TABLE 2

| | Change in activity of KTGB0202 bacteria during culture time | | | | |
|---|---|---|---|---|---|
| Culture time | Antifungal effect (mm) | Antiviral effect (%) | Powdery mildew control effect (%) | OD (660 nm) | pH |
| 0 | 0 | 0 | 0 | 0.012 | 7.70 |
| 6 | 0 | 0 | 0 | 0.063 | 7.65 |
| 12 | 0 | 0 | 12.5 | 0.644 | 7.19 |
| 24 | Weak | 0 | 75.0 | 0.758 | 6.88 |
| 48 | Weak | 0 | 75.0 | 0.919 | 7.22 |
| 72 | 12 | 50 | 75.0 | 0.780 | 6.75 |
| 96 | 13 | 60 | 87.5 | 0.578 | 6.79 |
| 120 | 13 | 67 | 87.5 | 0.471 | 6.62 |
| 144 | 11 | 85 | 87.5 | 0.525 | 6.70 |
| 168 | 11 | 76 | 100 | 0.468 | 6.72 |
| 192 | 10 | 82 | 87.5 | 0.433 | 7.09 |
| Tap water | 0 | 0 | 0 | — | — |

As can be seen in Table 2, the antifungal effect and the powdery mildew control effect were shown after 24 hours of culture, and the antiviral effect was shown after 72 hours of culture.

agar plug with a diameter of 0.6 mm. The agar plug was cultured with test plant pathogens on potato dextrose agar medium and then measured for clear distance so as to examine antifungal activity.

The measurement results for antifungal activity are shown in Table 4 below.

TABLE 4

Antifungal activity spectrum of KTGB0202 bacteria

| Pathogenic fungi | Antifungal activity (mm) |
|---|---|
| *Cladosporium fulvum* | 8 |
| *Colletotrichum gloeosporioides* | 6 |
| *Botrytis cinerea* | 2.5 |
| *Phytophthora capsici* | 10 |
| *Rhizoctonia solani* | 8 |
| *Fusarium oxysporum* | 5 |
| *Alternaria solani* | 4 |
| *Candida albicans* | 4 |

Test Example 4

Test of Control Effect of KTGB0202 Bacteria against Various Plant Diseases

The in vivo antifungal activity of KRGB0202 bacterial culture broth against *Magnaporthe grisea, Corticium sasaki, Botrytis cinerea, Phytophthora infestans, Puccinia recondita*, and *Blumeria graminis* was tested using seedlings of various crops.

The results are shown in Table 5 below.

TABLE 5

Test results for control effect of KTGB0202 bacterial culture broth against various plant diseases

| Plant pathogenic fungi | Control value (%) upon treatment with ten-fold-diluted culture |
|---|---|
| *Magnaporthe grisea* | 100 |
| *Corticium sasaki* | 85 |
| *Botrytis cinerea* | 71 |
| *Phytophthora infestans* | 97 |
| *Puccinia recondite* | 93 |
| *Blumeria graminis* | 95 |

As can be seen in Table 5, the KTGB0202 bacteria had an excellent control effect against various plant diseases.

Test Example 5

Test of Control Effect against Tobacco Powdery Mildew

Preventive and therapeutic effects against powdery mildew were measured on tobacco plants growing in pots under greenhouse conditions.

When the incidence of powdery mildew lesions on tobacco leaves was 10% or more, the tobacco leaves were treated with the culture broth of Example 2, and after 7 days of the final spreading, measured for incidence so as to determine the control effect of the KTGB0202 bacteria.

1. Test of Control Effect of KTGB0202 Bacteria Culture against Tobacco Powdery Mildew Tobacco plants growing in a greenhouse were treated with the culture of Example 2 so as to examine the disease development and therapeutic effects of the culture.

Examination of the thermal stability of culture active ingredients was performed after heating at 100° C. for 30 minutes, and the results are shown in Table 6 below.

TABLE 6

Test results for control effect of KTGB0202 bacteria against tobacco powdery mildew

| Tested substance | Incidence (%) | Control value (%) |
|---|---|---|
| Bacteria culture | 8.9 | 91.1 |
| Bacteria culture (thermal treatment) | 11.5 | 88.5 |
| Tap water | 100 | 0 |

As can be seen in Table 6, the control effect of the KTGB0202 bacteria culture against tobacco powdery mildew was an excellent value of 91%. Also, the loss of activity caused by thermal treatment was insignificant, indicating the thermal stability of the bacteria culture at high temperature.

2. Test of Control Effect of KTGB0202 Bacteria Culture against Tobacco Powdery Mildew at Various Diluted Concentrations The culture of Example 2 was diluted 10-fold to 100-fold with sterilized distilled water and examined for a control effect against tobacco powdery mildew.

Each of the dilutions was spread to leaves three times at five-day intervals, and after 7 days, the results were examined and shown in Table 7 below.

TABLE 7

Test results for control effect of KTGB0202 bacteria against tobacco powdery mildew at various dilution concentrations

| Dilution fold | Incidence (%) | Control value (%) |
|---|---|---|
| One-fold | 0 | 100 |
| Five-fold | 5.0 | 95.5 |
| Ten-fold | 12.5 | 87.5 |
| Twenty-fold | 25.0 | 75.0 |
| Fifty-fold | 45.7 | 55.0 |
| One hundred-fold | 67.5 | 32.0 |
| Tap water | 100 | 0 |

As can be seen in Table 7 above, the fifty-fold-diluted culture of the present invention showed a control effect of 55.0%, and when the undiluted culture was used, there was no occurrence of powdery mildew on the treated tobacco leaves.

3. Test of Control Effect of KTGB0202 Bacteria Culture Against Tobacco Powdery Mildew Using Various Treatment Methods A five-fold dilution of the KTGB0202 bacteria culture prepared in Example 2 was applied to the surface, back surface and both surfaces of tobacco leaves three times at five-day intervals, and after 7 days, the results were examined and shown in Table 8 below.

TABLE 8

Test results for control effect of KTGB bacteria culture against tobacco powdery mildew according to treatment methods

| | Incidence (control value (%)) | |
|---|---|---|
| Tested leaf-side | Surface | Back surface |
| Surface | 12.5 (87.5) | 50.0 (50.0) |
| Back surface | 100 (0) | 0 (100) |
| Surface/back surface | 12.5 (87.5) | 0 (100) |
| Tap water | 100 (0) | 100 (0) |

As can be seen in Table 8 above, the KTGB0202 bacteria culture when spread on the one surface of tobacco leaves showed a disease control effect of 50%, and when it was spread on both the surfaces of tobacco leaves, the most complete control effect was shown.

Test Example 6

Test of Control Effect of KTGB0202 Bacteria Culture against Strawberry Powdery Mildew In order to examine the control effect of KTGB0202 bacteria culture against strawberry powdery mildew, the KTGB0202 bacteria culture of Example 2 was spread to Maehyang strawberries growing in the Nonsan Strawberry Experiment Station located at Nonsan-shi, Chungcheongnam-do, Korea, three times at intervals of 6-7 days.

After 5-7 days of each treatment, the strawberries were harvested and examined for the incidence on leaves and the incidence on fruits, and the examination results are given in Tables 9 and 10, respectively.

TABLE 9

Test results for control effect of KTGB0202 bacteria against powdery mildew on strawberry fruits

| Treated content | 7 days after first spreading | | 5 days after second spreading | | 9 days after third spreading | |
|---|---|---|---|---|---|---|
| | Incidence (%) on fruits | Control value (%) | Incidence (%) on fruits | Control value (%) | Incidence (%) on fruits | Control value (%) |
| Ten-fold-diluted | 17.6 | 35.5 | 11.0 | 72.6 | 7.5 | 89.8 |
| Thirty-fold-diluted | 13.4 | 50.9 | 17.5 | 56.5 | 9.5 | 87.1 |
| Fifty-fold-diluted | 15.4 | 43.6 | 34.4 | 14.4 | 12.5 | 83.1 |
| Tap water | 27.3 | — | 40.2 | | 73.8 | — |

TABLE 10

Test results for control effect of KTGB0202 bacteria against powdery mildew on strawberry leaves

| Treated content | Incidence (%) | Control effect (%) |
|---|---|---|
| Ten-fold diluted culture | 2.45 | 96.5 |
| Thirty-fold diluted culture | 13.3 | 80.8 |
| Fifty-fold diluted culture | 20.4 | 70.5 |
| Tap water | 69.3 | — |

As can be seen in Tables 9 and 10, the disease development on fruits was controlled up to 89.8%, and the highest inhibitory effect against the disease development on leaves was 96.5%.

Test Example 7

Test of Control Effect of KTGB0202 Bacteria Culture against Pumpkin Powdery Mildew In order to examine the control effect of the KTGB0202 bacteria culture of Example 2 against pumpkin powdery mildew, the inventive culture was spread to pumpkin leaves with diffused powdery mildew, which have been growing in pumpkin cultivation farmhouses located at Kongju-shi, Chungcheongnam-do, Korea.

The KTGB0202 bacteria culture was spread three times at intervals of 3-4 days, and after 8 days, the incidence on the leaves was examined and shown in Table 11 below.

TABLE 11

Test results for control effect of KTGB0202 bacteria culture against pumpkin powdery mildew

| Tested substance | Incidence (%) | Control effect (%) |
|---|---|---|
| 10-fold-diluted culture | 2.5 | 97.4 |
| 30-fold-diluted culture | 4.5 | 95.3 |
| 50-fold-diluted culture | 10.5 | 89.2 |
| Tap water | 97.5 | — |

As can be seen in Table 11, the inventive bacteria culture showed a high control effect of 89.2-97.4% even though it was spread on the pumpkin leaves with severely disused disease. This suggests that the inventive bacteria culture is excellent in not only preventive effects but also therapeutic effects.

Test Example 8

Test of Control Effect of KTGB0202 Bacteria Culture against Cucumber Powdery Mildew The inventive culture was spread to cucumber leaves with a powdery mildew incidence of about 10%, which have been growing in pots under greenhouse conditions, and it was examined for a disease control effect on the cucumber leaves.

The inventive culture was spread three times at one-week intervals, and after 7 days, the incidence on the treated leaves was examined and shown in Table 12 below.

Also, Trifumin® (Triflumizole) was used at a 4000-fold-diluted concentration, a recommended concentration for farmhouses.

TABLE 12

Test results for control effect of KTGB0202 bacteria culture against cucumber powdery mildew.

| Tested substance | Incidence (%) | Control effect (%) |
|---|---|---|
| 10-fold-diiluted culture | 2.46 | 97.54 |
| 30-fold-diluted culture | 12.6 | 87.40 |

TABLE 12-continued

Test results for control effect of KTGB0202
bacteria culture against cucumber powdery mildew.

| Tested substance | Incidence (%) | Control effect (%) |
|---|---|---|
| Trifumin ® (Triflumizole) | 3.41 | 96.59 |
| Underground water | 100 | — |

As can be seen in Table 12 above, the ten-fold-diluted culture of the present invention showed an effect equal to the control chemical Trifumin®.

Test Example 9

Test of Control Effect of KTGB0202 Bacteria Culture against Melon Powdery Mildew The bacteria culture was spread to melons with a powdery mildew incidence of about 10% under greenhouse conditions three times at one-week intervals, and after 7 days, the results were examined.

Trifumin® and Fenari® (Fenarimol) were used at a 4000-fold-diluted concentration, a recommended concentration for farmhouses.

The number of leaves with melon powdery mildew was counted before and after treatment so as to yield therapeutic effects. The results are given in Table 13 below.

TABLE 13

Test results for control effect of KTGB0202
bacterial culture against melon powdery mildew

| Tested substance | Number of infected leaves before treatment/number of infected leaves after treatment | Therapeutic effect |
|---|---|---|
| 10-fold-diluted culture | 11/0 | 100 |
| 30-fold-diluted culture | 5/1 | 80 |
| Trifumin ® (Triflumizole) | 10/0 | 100 |
| Fenari ® (Fenarimol) | 9/6 | 33.4 |
| Tap water | 6/6 | 0 |

As can be seen in Table 13, the KTGB0202 bacteria culture showed an excellent control effect of 90-100%, and also an excellent inhibitory effect against disease development on fresh leaves, suggesting an excellent preventive effect as compared to the control chemical Trifumin®.

Test Example 10

Test of Control Effect of KTGB0202 Bacteria Culture against Tomato Powdery Mildew The KTGB0202 bacteria culture was spread three times at one-week intervals to the leaves of tomatoes with diffused disease, which have been growing in a tomato experiment station located at Buyeo-kun, Chungcheongnam-do, Korea. After 7 days, an inhibitory effect against disease development on the leaves was examined, and the results are shown in Table 14 below.

TABLE 14

Test results for control effect of KTGB0202
bacteria culture against tomato powdery mildew

| Tested substance | Incidence (%) | Control effect (%) |
|---|---|---|
| 10-fold-diluted culture | 4.43 | 95.57 |
| 30-fold-diluted culture | 10.52 | 89.48 |
| Tap water | 100 | 0 |

As can be seen in Table 14 above, even though the culture was spread on the tomato leaves with diffused disease, it showed an excellent-therapeutic effect of 89.48-95.57%.

Test Example 11

Test of Control Effect of KTGB0202 Bacteria Culture against Rose Powdery Mildew

In order to examine the control effect of the inventive KTGB0202 bacteria culture against rose powdery mildew, the KTGB0202 bacteria culture was spread to roses where rose powdery mildew (*Sphaerotheca pannosa*) has occurred. The results are given in Table 15 below.

TABLE 15

Test results for control effect of KTGB0202
bacteria culture against rose powdery mildew

| Tested substance | Leaf infection (%) | Control effect (%) |
|---|---|---|
| 40-fold-diluted culture | 2.3 | 97.9 |
| 80-fold-diluted culture | 6.0 | 93.9 |
| Untreated | 98.0 | — |

As can be seen in Table 15 above, the inventive KTGB0202 bacteria culture showed a very high control effect against rose powdery mildew.

Test Example 12

Test of Antifungal Activity of Antifungal Substance KTGB0202-AF01

The antifungal substance KTGB0202-AF01 of Example 3 was prepared.

The prepared KTGB0202-AF01 was dissolved in methanol to a concentration of 100 ppm, and buried in a paper disc with a diameter of 8 mm. Then, it was examined for a growth inhibitory effect against plant pathogenic fungi and *Candida albicans*.

The results are shown in Table 16 below.

TABLE 16

Test results for antifungal activity of
antifungal substance KTGB0202-AF01

| Pathogenic fungi | Antifungal activity (clear zone, mm) |
|---|---|
| *Cladosporium fulvum* | 12 |
| *Colletotrichum gloeosporioides* | 14 |
| *Phytophthora capsici* | 9 |
| *Botrytis cinerea* | 10 |
| *Rhizoctonia solani* | 11 |
| *Fusarium oxysporum* | 9 |
| *Alternaria solani* | 13 |
| *Candida albicans* | 12 |

As can be seen in Table 16, the antifungal substance KTGB0202-AF01 of the present invention showed antifungal activity.

INDUSTRIAL APPLICABILITY

The present invention provides the novel microorganism *Bacillus amyloliquefaciens* KTGB0202 bacteria, the KTGB0202 bacteria culture broth, and the antifungal substance KTGB0202-AF01 obtained by extraction and purification from the KTGB0202 bacteria culture.

The inventive KTGB0202 bacteria are used for controlling Powdery mildew, *Cladosporium* sp., *Colletotrichum* sp., *Phytophthora* sp., *Botrytis cinerea*, *Rhizoctonia solani*, *Fusarium* sp., *Alternaria* sp., *Magnaporthe grisea*, *Puccinia recondita*, *Corticium sasaki*, *Candida* sp., and the like.

Furthermore, the inventive KTGB0202 bacteria, the KTGB0202 bacteria culture broth and the antifungal substance KTGB0202-AF01 have a broad spectrum of antifungal activity, are excellent in activity continuance, physically and chemically safe, and mass-cultured in a short time, which suggests excellent economic efficiency.

What is claimed is:

1. A biologically pure *Bacillus amyloliquefaciens* KTGB0202 (accession number: KCTC 10564BP) having an antifungal activity against plant pathogenic fungi and an inhibitory effect against plant virus infection, the *Bacillus amyloliquefaciens* KTGB0202 comprising a nucleotide sequence;

gcaatgagcg ttatcgtatc ccgggcgctt ccggatgtgc gtgacggtct gaagccggtt 60
cacaggcgga ttttgtacgc aatgaatgat ttaggcatga ccagtgacaa accatataaa 120
aaatctgccc gtatcgtcgg tgaagttatc ggtaagtacc acccgcacgg tgactcagcg 180
gtttacgaat caatggtcag aatggcgcag gattttaact accgctacat gcttgttgac 240
ggacacggca acttcggttc ggttgacggc gactcagcgg ccgcgatgcg ttacacagaa 300
gcgagaatgt caaaaatcgc aatggaaatc ctccgggaca ttacgaaaga tacgattgat 360
tatcaagata actatgacgg cgcagaaaga gaacctgtcg tcatgccttc gagatttccg 420
aatctgctcg taaacggagc tgccggtatt gcggtcggaa tggcgacaaa tattcctccg 480

SEQUENCE LISTING

<160> NUMBER OF SEQ ID NOS: 1

<210> SEQ ID NO 1
<211> LENGTH: 963
<212> TYPE: DNA
<213> ORGANISM: Bacillus amyloliquefaciens

<400> SEQUENCE: 1

```
gcaatgagcg ttatcgtatc ccgggcgctt ccggatgtgc gtgacggtct gaagccggtt        60
cacaggcgga ttttgtacgc aatgaatgat ttaggcatga ccagtgacaa accatataaa       120
aaatctgccc gtatcgtcgg tgaagttatc ggtaagtacc acccgcacgg tgactcagcg       180
gtttacgaat caatggtcag aatggcgcag gattttaact accgctacat gcttgttgac       240
ggacacggca acttcggttc ggttgacggc gactcagcgg ccgcgatgcg ttacacagaa       300
gcgagaatgt caaaaatcgc aatggaaatc ctccgggaca ttacgaaaga tacgattgat       360
tatcaagata actatgacgg cgcagaaaga gaacctgtcg tcatgccttc gagatttccg       420
aatctgctcg taaacggagc tgccggtatt gcggtcggaa tggcgacaaa tattcctccg       480
catcagcttg gggaagtcat tgaaggcgtg cttgccgtaa gtgagaatcc tgagattaca       540
aaccaggagc tgatggaata catcccgggc ccggattttc cgactgcagg tcagattttg       600
ggccggagcg gcatccgcaa ggcatatgaa tccgacggg gatccattac gatccgggct       660
aaggctgaaa tcgaagagac atcatcggga aaagaaagaa ttattgtcac agaacttcct       720
tatcaggtga acaaagcgag attaattgaa aaaatcgcag atcttgtccg ggacaaaaaa       780
atcgaaggaa ttaccgatct gcgtgacgaa tccgaccgta acggaatgag aatcgtcatt       840
gagatccgcc gtgacgccaa tgctcacgtc attttgaata acctgtacaa acaaacggcc       900
ctgcagacgt ctttcggaat caacctgctg gcgctcgttg acggacagcc gaaggtacta       960
agc                                                                     963
```
catcagcttg gggaagtcat tgaaggcgtg cttgccgtaa gtgagaatcc tgagattaca 540
aaccaggagc tgatggaata catcccgggc ccggattttc cgactgcagg tcagattttg 600
ggccggagcg gcatccgcaa ggcatatgaa tccggacggg gatccattac gatccgggct 660
aaggctgaaa tcgaagagac atcatcggga aaagaaagaa ttattgtcac agaacttcct 720
tatcaggtga acaaagcgag attaattgaa aaaatcgcag atcttgtccg ggacaaaaaa 780
atcgaaggaa ttaccgatct gcgtgacgaa tccgaccgta acggaatgag aatcgtcatt 840
gagatccgcc gtgacgccaa tgctcacgtc attttgaata acctgtacaa acaaacggcc 900
ctgcagacgt ctttcggaat caacctgctg gcgctcgttg acggacagcc gaaggtacta 960 agc 963.

2. The *Bacillus amyloliquefaciens* KTGB0202 of claim 1, wherein the plant pathogenic fungus is one selected from powdery mildew, *Cladosporium* sp., *Colletotrichum* sp., *Phytophthora* sp., *Botrytis dinerea*, *Rhizoctonia solani*, *Fusarium* sp., *Alternaria* sp., *Magnaporthe grisea*, *Puccinia recondita*, *Corticium sasaki*, and *Candida* sp.

3. The *Bacillus amyloliquefaciens* KTGB0202 of claim 2, wherein the powdery mildew is one selected from *Sphaerotheca fuliginea* of gourd plants, *S. humuli* of strawberry, *S. pannosa* of rose, *Erysiphe tabacina* of tobacco, *Leveillula taurica* and *Erysiphe cichoracearum* of Solanaceae vegetables, *Leveillula heraclei* of carrots, and *Blumeria graminis* of barley.

4. The *Bacillus amyloliquefaciens* KTGB0202 of claim 1, wherein the plant virus is tobacco mosaic virus (TMV).

5. A method for controlling plant pathogens using the *Bacillus amyloliquefaciens* KTGB0202 culture of claim 1.

* * * * *